(12) United States Patent
Burg et al.

(10) Patent No.: US 8,444,706 B2
(45) Date of Patent: May 21, 2013

(54) OXIDIZING COMPOSITION FOR THE TREATMENT OF KERATIN FIBERS

(75) Inventors: Wilfried Burg, Groβ-Gerau (DE); Matthias Morand, Bad Soden (DE); Anette Sallwey, Dreieich (DE); Manfred Schmitt, Bensheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/556,511

(22) Filed: Jul. 24, 2012

(65) Prior Publication Data

US 2012/0288459 A1  Nov. 15, 2012

Related U.S. Application Data

(63) Continuation of application No. 13/111,603, filed on May 19, 2011, now Pat. No. 8,308,822.

(30) Foreign Application Priority Data

May 19, 2010 (EP) .................................. 10163272

(51) Int. Cl.
*D06L 3/00* (2006.01)

(52) U.S. Cl.
USPC .................. 8/101; 8/107; 8/109; 8/110; 8/111

(58) Field of Classification Search
USPC .............................. 8/101, 107, 109, 110, 111
See application file for complete search history.

(56) References Cited

U.S. PATENT DOCUMENTS

| | | | |
|---|---|---|---|
| 4,159,253 A | 6/1979 | Grier | |
| 5,698,186 A | 12/1997 | Weeks | |
| 5,891,423 A | 4/1999 | Weeks | |
| 6,063,857 A | 5/2000 | Greenblat | |
| 6,547,833 B2 | 4/2003 | Casperson | |
| 6,984,268 B2 | 1/2006 | Pohl | |
| 7,041,142 B2 | 5/2006 | Chan | |
| 7,045,493 B2 | 5/2006 | Wang | |
| 7,066,968 B2 | 6/2006 | Chan | |
| 7,070,769 B2 | 7/2006 | Ascione | |
| 7,766,976 B2 | 8/2010 | Bureiko | |
| 2002/0152556 A1 | 10/2002 | Ascione | |
| 2002/0157191 A1 | 10/2002 | Casperson | |
| 2005/0191251 A1 | 9/2005 | Kravtchenko | |
| 2007/0033743 A1 | 2/2007 | Kravtchenko | |
| 2007/0033744 A1 | 2/2007 | Kravtchenko | |
| 2009/0270303 A1* | 10/2009 | Sunder et al. | 510/372 |

FOREIGN PATENT DOCUMENTS

WO    2006105853 A1    10/2006

OTHER PUBLICATIONS

Aculyn 28 Rheology Modifier/Stabilizer, 11 pages, (2004).
Carbopol Ultrez 21 Polymer product specification, 1 page, (2003).

(Continued)

*Primary Examiner* — Eisa Elhilo
(74) *Attorney, Agent, or Firm* — James T. Fondriest

(57) ABSTRACT

The present invention relates to an oxidizing composition for treatment of keratin fibers comprising a combination of; (a) at least one anionic associative copolymer, (b) at least one anionic non associative copolymer; (c) at least one peroxide agent; (d) at least one persulfate agent; (e) at least on alkalizing agent; and (f) a carrier medium suitable for hair treatment. The oxidizing composition described is suitable for composition used in conventional hair treatments such as dyeing, bleaching, and permanent waving or relaxing/straightening of the keratinous fibers, particularly human hair, requiring an oxidizing composition.

13 Claims, 3 Drawing Sheets

OTHER PUBLICATIONS

Premulen TR-1 Polymeric Emulsifier product specification, 1 page, (1997).
Carbopol ETD 2020 Polymer for Personal Care Applications technical data sheet, 2 pages, (2002).
Carbopol Ultrez 21 Polymer technical data sheet, 4 pages, (2002).

Lisa Eiton et al; "Application of Acrylates/Methacrylates/Beheneth-25 Methacrylate copolymer (Aculyn, 28) as a Thickner and Suspending Agent in Cosmetic Formulations and as a Polymeric Emulsifier"; Research Disclosure, Mason Publications; vol. 428, No. 1; Dec. 1, 1999.

* cited by examiner

OXIDIZING COMPOSITION FOR THE TREATMENT OF KERATIN FIBERS

CROSS REFERENCE TO RELATED APPLICATION

This application is a continuation application of prior U.S. application Ser. No. 13/111,603 filed May 19, 2011 now a U.S. Pat. No. 8,308,822 B2.

FIELD OF THE INVENTION

According to a first aspect the present invention relates to an oxidizing composition resulting from mixing a bleach powder and a peroxide developer for the treatment of keratin fibers comprising a combination of; (a) at least one anionic associative copolymer; (b) at least one anionic non associative copolymer; (c) at least one peroxide agent; (d) at least one persulfate agent; (e) at least on alkalizing agent; and (f) a carrier medium suitable for hair treatment.

According to a second aspect, the present invention relates to the use of the oxidizing composition as described above for providing maintained consistent rheology of said composition for the duration of the hair treatment.

According to a third aspect, the present invention relates to the use of the oxidizing composition as described hereinabove to minimize the swelling behaviour observed in described conventional oxidizing compositions.

According to a fourth aspect, the present invention relates to a method of applying the oxidizing composition as described hereinabove in order to maintain consistent rheology and minimize the swelling behaviour of said composition during the hair treatment; said method comprising the steps of: (i) providing a first peroxide developer composition comprising at least a peroxide agent and a combination of at least one anionic associative copolymer and at least one anionic non associative copolymer, and a carrier medium and; (ii) providing a second bleach powder mixture comprising at least one persulfate agent, an alkalizing agent, and a carrier medium; (iii) mixing the composition described in (i) and the composition in (ii) together, and (iv) applying the composition described in (iii) onto the keratin fibers, especially hair, without the necessity to vigorously mix the total composition during the application in order to maintain the appropriate viscosity and minimizing the swelling behaviour.

According to a fifth aspect, the present invention relates to an oxidizing composition kit comprising; (i) a first separately packaged composition comprising at least one peroxide agent and a combination of at least one anionic associative copolymer and at least one anionic non associative copolymer and a carrier medium; (ii) and a second composition comprising at least one persulfate agent, at least one alkalizing agent and a carrier medium.

BACKGROUND OF THE INVENTION

The present invention relates to an oxidizing composition for treatment of keratin fibers comprising a combination of;
(a) at least one anionic associative copolymer,
(b) at least one anionic non associative copolymer;
(c) at least one peroxide agent;
(d) at least one persulfate agent;
(e) at least on alkalizing agent; and
(f) a carrier medium suitable for hair treatment.

Conventional hair treatments such as dyeing, bleaching, and permanent waving or relaxing/straightening of the keratinous fibers, particularly human hair always require an oxidizing composition.

Human hair, mainly constituted by a-keratins is a sturdy and insoluble structure. One of the explanations for the strength and rigidity conferred to the keratin fibers present in the hair is the presence of large amounts of di-sulfur bridges formed with sulfur-containing amino acid cystein.

The actual role of the oxidizing composition can be multiple depending on the type of treatment. In hair colouring the role of the oxidizing composition is to decolorize the melanin pigment, lightening the underlying colour of the hair. But most important is its role to couple together the dye precursors to form the colored chromophores in the hair. For example, its major role in hair dyeing is to oxidize the dye precursors, which then being "activated" allows the cascade of reactions terminating with the formation of the hair dye. When used in hair bleaching, the oxidizing composition also has the role of gradually destroying the two natural pigments (eumelanins (brownish black) and pheomelanins (reddish orange)) embedded throughout the cortex. The characteristic natural gradation of the colour of human hair is the result of the combination of the ratio and concentration of these types of pigments. For example, while dark hair shows a higher concentration of the eumelanins, red hair shows a predominance of the pheomelanins. Light blond hair has reduced amounts of both. Experience has also shown that when aimed to be used to destroy the natural pigment of the hair, the oxidizing composition also destroys both eumelanin and pheomelanin, but at a different rate. Indeed, it has been found that the eumelanins are easier to break down than the pheomelanins. Because of these two different rates of destruction, dark hair when bleached leads to an undesirable warm reddish orange or "brassy" tone due to the enhancement of the red pigments. Finally, when used in hair bleaching the oxidizing composition also has to bleach previously deposited synthetic colour already present in the hair.

When typically used as a dye precursor activator in a hair dyeing system, the oxidizing composition mainly contains a peroxide agent in a concentration ranging from 0.6% to 10% on head by weight relative.

On the other hand, when used as melanin and synthetic colour destructor, the oxidizing composition present in the final hair treatment mixture would be typically provided from a peroxide developer comprising a peroxide agent in a concentration ranging of from 1.5% to 12.0%, by weight relative to the peroxide developer and a bleach powder comprising a persulfate agent at a concentration ranging from 10.0% to 40.0% of active oxygen ($S_2O_8^{2-}$) by weight relative to the bleach powder. Thus, the on head concentration of peroxide agent is typically 0.6% up to 10% for the peroxide agent and from 2.0% to 27% for the persulfate concentration by weight relative to the oxidizing composition (i.e. after mixing of the bleach powder and the peroxide developer at a 2:1 up to 1:4 ratio.

Being highly chemically reactive, the oxidizing composition, besides the role attributed to them, may also impact on the carrier medium of the hair treatment composition, undergoing some undesired side reactions. These reactions may have an impact on the different physical properties of the final hair treatment composition, such as the consistency and the homogeneity.

In order to be conveniently used by the consumer or stylist, the active agents, such as the oxidizing composition of the hair treatments are included in a carrier medium comprising various components, such as polymers, surfactants, stabilizers, chelants and aqueous carrier. These various additional components are important and necessary in order to obtain a composition providing the desired benefit to the consumer, with the actives principles but also enabling the consumer to use this composition conveniently without any harm.

Compounds known as "rheology modifiers" are crucial for any cosmetic composition, as they drive the necessary consistency for the composition, enabling the consumer to handle the composition and obtain the benefit. When exposed to an oxidizing environment, the rheology modifiers have an extra challenge of having to be chemically and physically stable to this highly reactive environment.

A rheology modifier enabling the maintenance of the physical stability of an oxidizing composition is described in U.S. Pat. No. 7,070,769 B2, wherein a composition comprising "at least two anionic associative polymers" is described. Also U.S. Pat. No. 6,547,833 B2 describes "a high aqueous-content developer formulation for use in a two-part composition for oxidative dyeing of hair, the developer formulation comprising at least about 70% by weight water, a peroxide oxidizer, and an acrylate/beheneth-25 methacrylate copolymer (Aculyn 28).

An object of the present invention is to provide an oxidizing composition suitable for the chemical treatment of keratinous material, such as, for example, dyeing, bleaching, relaxing, and permanent waving of keratinous fibers.

Among all the criteria required for a hair treatment composition, one very important criteria is the obtention of the desired consistency/rheology, or texture. This criteria is essential to allow the consumer an easy application of the hair treatment composition. In order to provide this easy application of the hair treatment, compounds giving a "thickening" benefit are used.

The main quality of a good rheology modifier is to be able to give the desired consistency when the final composition is prepared, during the treatment and until the end just before the consumer or stylist removes it from the hair. As well as having the desired consistency/rheology during the preparation of the final composition, a highly desirable rheology modifier would also maintain this consistency/rheology during the application of the composition onto the hair, until the end of the treatment process.

Usually, it has been found that the performance of the rheology modifier is highly correlated with the amount and type of oxidizing agent. As mentioned above, because of the highly chemical reactivity of the oxidizing agent, it is challenging to find effective rheology modifiers providing this benefit during the whole period of the hair treatment without a decrease of its performance due to interactions with the oxidizing agent present in the media; i.e. a great stability among all the other components of the composition. Thus until now, the only means to overcome this problem of maintaining the same consistency/rheology was to continuously and vigorously stir the oxidizing composition during application. This is inconvenient for the stylist and the consumer and results in an increase in the time required to apply the product to the hair.

Whilst not being bound by theory, the rational explanation for the alteration of the rheology and consistency profile during use is related to the observed phenomenon of "puffing up" or "foaming" or "swelling" behaviour of a typical oxidizing composition after mixing of the components. This is believed to be related to the reactions occurring during mixing which tend to provide in situ the formation of gas, such as $O_2$ or $CO_2$, which may be responsible for the swelling of the total composition. The bubbles of gas trapped in the composition may be released by applying a vigorous agitation to the composition.

This swelling behaviour of the final composition is a drawback, because it impacts the consistency of the final composition. Practically, having less compact and less dense properties, the composition would exhibit some difficulties for the consumer or stylist when applying the composition on the hair. Therefore some of the oxidizing composition when applied on consumer hair would have the tendency to drip or to fall off the hair, leading to a very difficult application of the hair-product. Much more critical are the swelling behaviours on hair after the application and during the development time because the swelling behaviour leads to expanded (bloated) foil packs or unlikely colouring effects on untreated hair when using free hand techniques.

Indeed conventional rheology modifiers, especially those involved in oxidizing compositions, tend to give a swelling side-effect when the components of said oxidizing composition comprise a persulfate agent, a peroxide agent and alkalizing agents. Depending on the amount of the alkali persulfate agent, the peroxide agent and the alkalizing agents present in the oxidizing composition used in the hair treatment, this results in swelling of the oxidizing composition. This foaming phenomenon is particularly excessive in the case of highly oxidative environments, such as bleaching compositions.

Particularly, in the field of hair treatment which uses oxidizing compositions (i.e. bleaching, dyeing, permanent waving or relaxing/straightening of the keratinous fibers, particularly human hair) there remains the need to have an effective rheology modifier, which is stable, and inert towards the active principles as well as the other components of the oxidizing composition. As well as stability as an essential characteristic for an acceptable rheology modifier, it is also desirable to identify a rheology modifier, which prevents the foaming behaviour observed for oxidizing compositions and overcomes the swelling behaviour.

In the present invention an oxidizing composition is described, which as well as providing a highly desirable property of maintaining the rheology of the composition during the hair treatment, also provides an effective decrease of the swelling behaviour of the oxidizing composition. Thus, the oxidizing composition of the present invention facilitates easy application of the composition to the hair and a very good adherence on the hair from the start application until the end of the hair treatment.

It has now been found that the specific combination of an anionic associative and an anionic non associative polymer used in an oxidative environment, as well as providing an excellent rheology performance, chemical and physical stability, also provides an effective decrease of the undesirable swelling behaviour observed in the oxidizing composition with other rheology modifiers. This specific combination has been found to provide excellent results, particularly with the so-called "Balayage technique", where hair color is painted directly onto sections of the hair with no foils used to keep the color contained.

SUMMARY OF THE INVENTION

Figure 1A:
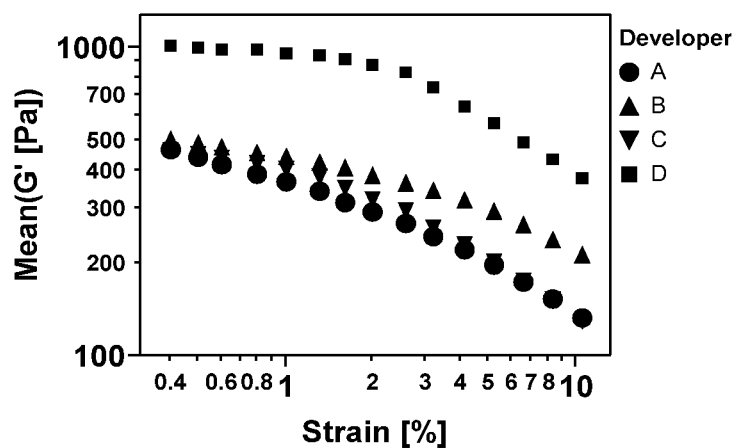
FIG. 1a shows a graphical representation of strain sweep curves resulting from a combination of bleach 1 and developers A, B, C and D.
Figure 1B:
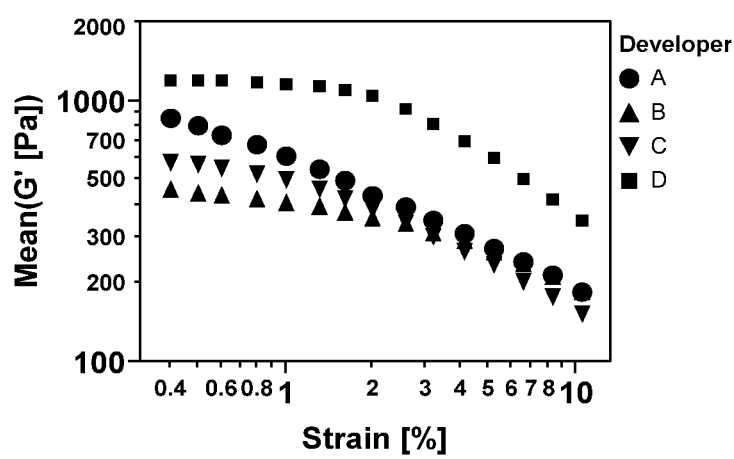
FIG. 1b shows a graphical representation of strain sweep curves resulting from a combination of bleach 2 and developers A, B, C and D.

According to a first aspect the present invention relates to an oxidizing composition resulting from mixing a first peroxide developer and a bleach powder composition for the treatment of keratin fibers comprising a combination of;
(a) at least one anionic associative copolymer,
(b) at least one anionic non associative copolymer;
(c) at least one peroxide agent;
(d) at least one persulfate agent;
(e) at least on alkalizing agent; and
(f) a carrier medium suitable for hair treatment.

In the present invention the term oxidizing composition means a composition which is the result of a mixture of two compositions namely a bleach powder and a peroxide developer. The definitions for both these terms are as follows.

In the present invention the term peroxide developer means a composition comprising (a) at least one anionic associative copolymer, (b) at least one anionic non associative copolymer; (c) at least one peroxide agent; and (f) at least a carrier medium suitable for hair treatment.

In the present invention the term bleach powder means a composition, preferably a solid powder comprising (d) at least one persulfate agent; (e) at least on alkalizing agent; and (f) a carrier medium suitable for hair treatment.

In the present invention the pH value of the peroxide developer is in a range of from 2.0 to 5.5, preferably from 2.5 to 4.0.

In the present invention the bleach powder contains an alkalizing agent (e) in a range of from 5% to 30%, preferably from 8% to 25% to enable, once mixed with the peroxide developer to obtain an oxidizing composition with a pH in the range of from 8.5 to 13, more preferably from 9.0 to 11.

In the present invention, the carrier medium (f) will comprise the remaining components commonly added into hair treatment compositions such as bleaching and/or dyeing particularly of the keratinous fibers, particularly human hair. It should be noted that components belonging to the carrier medium may be present in both the bleach powder composition and the peroxide developer composition. The dispersion of the components classified as "medium carrier" will depend upon their stability and role in each of these compositions (bleach powder and peroxide developer).

The term oxidizing composition as used in the present invention refers to compositions which can be used in bleaching and/or dyeing and/or permanent waving and/or relaxing/straightening of the keratinous fibers, particularly human hair.

According to a second aspect, the present invention relates to the use of the oxidizing composition as described above for providing maintained consistent rheology of said composition for the duration of the hair treatment.

According to a third aspect, the present invention relates to the use of the oxidizing composition as described hereinabove to minimize the swelling behaviour observed in described conventional oxidizing compositions.

According to a fourth aspect, the present invention relates to a method of applying the oxidizing composition as described hereinabove in order to maintain consistent rheology and minimize the swelling behaviour of said composition during the hair treatment; said method comprising the steps of:
(i) providing a first peroxide developer mixture comprising at least a peroxide agent and a combination of at least one anionic associative copolymer and at least one anionic non associative copolymer, a carrier medium and;
(ii) providing a second bleach powder mixture comprising at least one persulfate agent, an alkalizing agent, a carrier medium;
(iii) mixing the composition described in (i) and composition in (ii) together, and
(iv) applying the composition described in (iii) onto the keratin fibers, especially hair, without the necessity to mix vigorously the total composition during the application in order to maintain the appropriate viscosity and minimizing the swelling behaviour.

According to a fifth aspect, the present invention relates to an oxidizing composition kit comprising;
(i) a first separately packaged peroxide developer composition comprising at least one peroxide agent and a combination of at least one anionic associative copolymer and at least one anionic non associative copolymer and a carrier medium;
(ii) and a second bleach powder composition comprising at least one persulfate agent, at least one alkalizing agent and a carrier medium.

DETAILED DESCRIPTION OF THE INVENTION

According to a first aspect the present invention relates to an oxidizing composition resulting from mixing a bleach powder and a peroxide developer for treatment of keratin fibers comprising a combination of;
(a) at least one anionic associative copolymer,
(b) at least one anionic non associative copolymer;
(c) at least one peroxide agent;
(d) at least one persulfate agent;
(e) at least on alkalizing agent; and
(f) a carrier medium suitable for hair treatment.

In this invention is described an oxidizing composition comprising a rheology modifier compatible and stable in an oxidative environment. Indeed it has been found that a particular combination of two specific copolymers, besides the role of thickening the oxidizing composition when added to the oxidizing composition; also enable the maintenance of the same consistency during the whole process of the hair treatment.

As well as providing an acceptable rheology profile and stability during the treatment, another key aspect of the present invention is to provide a rheology modifier with the highly desirable property of maintaining the rheology of the composition during the hair treatment.

Peroxide Developer

In the present invention the term peroxide developer means a composition comprising (a) at least one anionic associative copolymer, (b) at least one anionic non associative copolymer; (c) at least one peroxide agent; and (f) at least a carrier medium suitable for hair treatment.

The anionic associative polymers are amphiphilic polymers comprising at least a hydrophilic portion as a backbone connected to each side with an hydrophobic portion as side chains, according to the following formula (I):

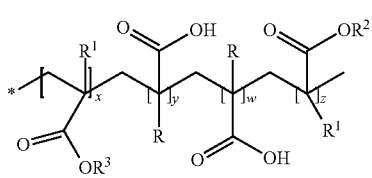

Formula (I)

$R^2, R^3$ = acyl chain
R = O (acrylic acid unit), or R = $CH_3$ (methacrylic acid unit)
or R = $C_2H_5$ (ethacrylic acid unit),
or R = $CH_2COOH$ (itaconic acid)

The hydrophilic backbone comprises at least an acrylic acid unit (R=O), and/or at least a methacrylic acid unit (R=$CH_3$) and/or at least an itaconic acid unit (R=$CH_2COOH$), and mixtures thereof. The hydrophilic backbone comprises preferably at least an acrylic acid unit (R=O), and at least a methacrylic acid unit (R=$CH_3$).

The anionic associative copolymer comprises a monomer having a carboxylic acid function and a monomer having an ester derived from a fatty alcohol (C4-C30) and a carboxylic acid.

The hydrophobic units comprise the corresponding esters of the hydrophilic portion; i.e. at least acrylate ester unit ($R^1$=O), and/or at least a methacrylate ester unit ($R^1$=$CH_3$) and/or at least an itaconate ($R^1$=$CH_2COOR^5$, wherein $R^5$ is C1-C30), and mixtures thereof. The hydrophobic backbone comprises preferably at least an acrylate ester unit ($R^1$=O), and at least a methacrylate ester unit ($R^1$=$CH_3$).

The ester units of the hydrophobic units comprise substituents $R^2$ and $R^3$ being a polethylenoxylene glycol ether of fatty alcohol, falling with the following general formula:

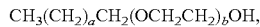

Wherein a is a mixture of C1-C18, and/or a mixture of C1-C20, and/or a mixture of C1-C22, and/or a mixture of C1-C24, a is preferably a mixture of C1-C20, i.e. behenyl alcohol, which consists chiefly of n-docosanol ($CH_2(CH_2)_{20}CH_2OH$).

Wherein b has an average value of 20.

Representative anionic amphiphilic polymers that can be used may further be cross-linked. The crosslinking agent can be a monomer comprising a group (IV)

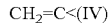

with at least one other polymerizable group whose unsaturated bonds are not conjugated with respect to one another. Mention may be made, for example, of polyallyl ethers such as polyallylsucrose and polyallyl pentaerythritol.

Suitable materials include materials sold under trade name Aculyn 28 by the company Rohm & Haas, materials sold under trade names Permulen TR1, Carbopol 2020, Carbopol Ultrez-21 by the company Noveon, and materials sold under the trade names Structure 2001 and Structure 3001 by the company National Starch.

The peroxide developer composition may comprise from 0.1% to 10%, preferably from 0.2% to 6% more preferably from 0.5% to 2% by weight of said anionic associative polymer relative to the peroxide developer composition.

The anionic non associative polymer are also amphiphilic polymers comprising at least a hydrophilic portion as a backbone connected to each side with an hydrophobic portion on one side only, according to the following formula (II):

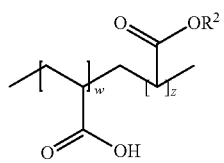

Formula (II)

The hydrophilic backbone and hydrophobic units forming the anionic non associative polymer are synthesized from acid and acrylate co-monomers and made through emulsion polymerisation. The anionic non associative copolymer comprises at least a monomer having a carboxylic function and at least a monomer having an ester derived from an alkoxylated fatty (C4-C30) alcohol and carboxylic acid.

Suitable anionic non-associative polymers for use herein can be chosen, for example, from:
(i) cross-linked acrylic acid homopolymers;
(ii) copolymers of acrylic or (meth)acrylic acid and of C1-C6 alkyl acrylate or (meth)acrylate.

Preferable polymers are the products sold under the names Carbopol 980, 981, 954, 2984, 5984 by the company Noveon or the products sold under the names Synthalen M, Synthalen L and Synthalen K by the company 3V Sigma, or the product sold under the name Aculyn 33 by the company Rohm and Haas. Most preferably the anionic non associative polymer is Aculyn 33.

The peroxide developer composition may comprise from 0.1% to 10%, preferably from 0.2% to 6% more preferably from 0.5% to 2.0% by weight of said anionic non associative polymer relative to the peroxide developer composition.

The peroxide developer composition of the present invention comprises a combination of said one anionic associative copolymer and said at least one anionic non associative copolymer preferably at a ratio ranging respectively from [5/1] to [1/5], more preferably from [3/1] to [1/3], more preferably from [2/1] to [1/2].

After mixing with the bleach powder composition, the resultant mixed oxidizing composition of the present invention will preferably comprise a combination of at least one anionic associative copolymer and at least one anionic non associative copolymer each independently in an amount ranging comprise from 0.01% to 8%, preferably from 0.05% to 5% more preferably from 0.15% to 2% by weight of said anionic associative polymer and said anionic non associative polymer relative to the total weight of the oxidizing composition.

The peroxide developer further comprises a peroxide agent (c). The peroxide developer contains a sufficient amount of peroxide agent such as hydrogen peroxide capable of lightening keratin fibers, such as hair to the desired level. Preferably, the peroxide developer comprises a peroxide agent in a concentration ranging from 1.5% to 12.0%, more preferably from 6% to 12% by weight relative to the total weight of the developer composition. Thus, the on head concentration of peroxide will be from 0.6% to 10% by weight for the hydrogen peroxide.

Suitable peroxide agents for use herein include hydrogen peroxide, urea peroxide, melamine peroxide or combinations of thereof.

In addition to the components described herein above, the peroxide developer may comprise additional ingredients to facilitate its use and performance. Thus, the peroxide developer composition may further comprise one or more of the following adjuvants: additional rheology modifiers (e.g.

waxes), antifoam agent, emulsifier, stablising agent, pH regulator, chelant, coloring agent, conditioning agent and/or fragrance. Each of these constituents is present in the peroxide developer in sufficient amount to provide its intended function in the peroxide developer composition or in the final product mixture when the peroxide developer is mixed with the bleach powder. Suitable adjuvants are those that are stable to peroxide agent.

Suitable emulsifiers for use in the peroxide developer are typically in the range of from 0.05% to 10% preferably from 0.1% to 5%, especially from 0.5% to 2.5% by weight of the developer composition. Suitable emulsifiers are glyceryl stearate, oleth 2, oleth-10, PEG-75 lanolin, ceteareth-20 and mixtures thereof. The emulsifiers, which are surface active agents, may also contribute to thickening of the composition. Other suitable emulsifiers are identified the CTFA Ingredient Dictionary and Handbook, v. 2, at pages 1795-1803.

The peroxide developer composition may further contain for example an antifoam material such as dimethicone, to prevent foaming during manufacture; an acidifying material and or a preservative. Conventional hair conditioning agents may also be incorporated in the developer if compatible at the acidic conditions and in the presence of a peroxide agent.

The pH of the peroxide developer is generally in the range of from 2.0 to 5.5, preferably from 2.5 to about 4.

The peroxide developer composition is typically in the form of a liquid, cream or gel. Preferably the peroxide developer is in the form of a liquid to facilitate mixing with the bleach powder and typically has a viscosity of from 50 to 3000 mPas, most preferably from 100 to 1000 mPas as measured by Haake Rheometer VT 550 MV-Din 25° C. 64.5 l/s.

Bleach Powder

According the present invention the oxidizing composition comprises a bleach powder which comprises at least one persulfate agent, at least one alkalising agent and a carrier medium.

The persulfate agent (d) contains a sufficient amount of a persulfate e.g. as ammonium persulfate capable of lightening keratin fibers, such as hair to the desired level. Suitable persulfate agents for use herein include persulfate, perborate, percarbonate or combination of thereof. These are typically provided as the alkali salts. Preferred are potassium persulfate, sodium persulfate, ammonium persulfate and mixtures thereof.

The bleach powder composition of the present invention comprises at least one persulfate agent which is present in the oxidizing composition in a concentration ranging from 10.0% to 40.0% ($S_2O_8^{2-}$), by weight relative to the total weight of the oxidizing composition. Thus, the on head concentration of the persulfate agent will be from 2.0 to 30%. ($S_2O_8^{2-}$) based upon a 2:1 up to 1:4 mixing ratio.

The bleach powder further contains an alkalizing agent to ensure an alkaline bleach product when the bleach powder is mixed with the developer. The pH is preferably adjusted with alkali metal or alkaline earth metal salts that are alkaline in aqueous solution, enabling the final hair treatment to reach a pH of a range of from about 8.5 to about 13, especially about 9 to about 11. Suitable Alkali metal or Alkaline earth metal salts are Sodiumcarbonate, Sodiumhydrogencarbonate, Magnesiumcarbonate, Ammoniumcarbonate, Ammoniumhydrogencarbonate, Sodiumsilicate and/or mixtures thereof; present in the bleach powder component in an amount of from about 5 to about 30% by weight of the bleach powder composition component, preferably from about 7 to 25% by weight.

The bleach powder may also comprise additional adjuvant(s). In one embodiment the bleach powder may comprise a colorant selected from the group consisting of water insoluble pigments or lakes (and mixtures thereof (hereinafter "pigment"), generally in an amount of up to 2.5% by weight of the bleach powder, preferably from 0.1% to 2% by weight. The pigment should be compatible with the other ingredients in the oxidizing composition, and in particular it should be compatible with the peroxide agent. The pigments are colouring the oxidising composition only. Suitable pigments include ultramarine blue, D & C yellow No. 10 aluminum lake, chromium oxide green, D & C Red No. 30 lake, and D & C yellow No. 5 zirconium lake.

A dessicant such as silica is also typically incorporated to prevent moisture from prematurely reacting with the persulfates. The silica is a positive amount generally less than 5% by weight, usually from 0.01% to 3% by weight of the bleach powder. Additionally silica is acting as a lubricant to assist in dry blending of the powder materials.

In addition to the components described herein above, the bleach powder may comprise additional ingredients to facilitate its use and performance. Thus, the bleach powder composition may further comprise one or more of the following adjuvants: additional rheology modifiers (e.g. celluloses and starches), emulsifier, stabilising agent and/or chelant, de-dusting agents, conditioning agent, fragrance and/or dyes.

Each of the adjuvant constituents is present in the bleach powder in a sufficient amount to provide its intended function in the bleach powder or in the final product mixture when mixed with the peroxide developer.

Additional Components

According to the present invention the oxidising composition may comprise an additional alkalizing agent which is not compatible with the bleach powder components and is thus stored separately there from. Suitable compounds include ammonium hydroxide or other ammonia based alkalizing agents or monoethanolamine or ammonia based alkalizing agent.

The composition may further comprise dyes. Suitable dyes for use herein are those which are compatible with the components of the present invention and include dyes selected from the group consisting of azo dyes, quinone dyes, triphenylmethane dyes, acid dyes, basic dyes and nitro dyes.

These dyes are typically provided in the bleach powder and the total amount of the afore-said direct dyes in the bleach powder is from about 0.001 to 10 weight percent and preferably from 0.002 to 8 weight percent relative to the weight of the bleach powder. The concentration of these direct dyes in the ready-to-use oxidizing composition is from about 0.0004 to 5.5 weight percent.

Useful direct dyes for the attainment of the desired color shades are common, and physiologically harmless dyes resistant to peroxy salts may be selected from the group consisting of azo dyes, quinone dyes, triphenylmethane dyes, acid dyes, basic dyes and nitro dyes or a combination thereof, for example: 3-(2',6'-diaminopyridyl-3'-azo)pyridine {=2,6-diamino-3-[(pyridin -3-yl)azo]pyridine}; 2-[(4-ethyl-(2-hydroxyethyl)amino]-2-methylphenyl)-azo]-5-nitro-1,3-thiazole (Disperse Blue 106); N,N-di(2-hydroxyethyl)-3-methyl4-[(4-nitro-phenyl)azo]aniline (Disperse Red 17, CI 11210); 3-diethylamino-7-(4-dimethylamino-phenylazo)-5-phenylphenazinium chloride (CI 11050); 4-(2-thiazolylazo) resorcinol; sodium 4-[(4-phenylamino)azo]benzenesulfonate (Orange IV); 1-[(3-aminopropyl)amino-9, 10-anthracenedione (HC Red No. 8); 3',3'',4,5,5',5'',6,7-octabromophenolsulfonephthalein (Tetrabromophenol Blue); 1-[(4-amino-3,5 -dimethylphenyl)-(2,6- dichlorophenyl)methylene]-3,5-dimethyl-4-imino-2,5-cyclohexadiene phosphoric acid (1:1) (Basic Blue 77); 3',3'',5',5''-tetrabromom-cresolsulfonephthalein; disodium 2,4-dinitro-1-naphthol-7-sulfonate (Acid Yellow 1; CI 10 316); sodium 4-[(2'-hydroxy-1'-naphthyl)azo]benzenesulfonate (Acid Orange 7; CI 15 510); 3',6'-dihydroxy-2',4',5',7'-tetraiodospiro[isobenzofuran-1(3H),9'(9H)-xanthene]-3-one disodium salt (Acid Red 51; CI 45 430); disodium 6-hydroxy-5-[(2-methoxy-5-methyl-4-sulfophenyl)azo]-2-naphthalenesulfonate (FD&C Red 40; CI 16035); 2,4-dinitro-1-naphthol sodium salt (Acid Yellow 24; CI 10315); 2',4',5',7'-tetrabromo-4,5,6,7-tetrachloro-3',6'-dihydroxyspiro[isobenzofuran-1(3H),9'(9H) xanthene]-3-one disodium salt (Acid Red 92; CI 45410); sodium 4-(2-hydroxy-1-naphthylazo)-3-methyl-benzenesulfonate (Acid Orange 8; CI 15575); 2-amino-1,4-naphtalenedione; dithizone (1,5-diphenyl-thiocarbazone); N-(2-hydroxyethyl)-2-nitro-4-(trifluoromethyl)aniline (HC Yellow 13); N-(2-hydroxyethyl)-4-nitroaniline and 4-chloro-N-(2,3-dihydroxypropyl)-2-nitroaniline.

Other constituents of the oxidizing composition of the invention are, in general, surfactants and emulsifiers from the group of anionic, nonionic or ampholytic surface-active compounds, for example fatty alcohol sulfates, alkane sulfonates, olefin sulfonates, fatty alcohol polyglycol ether sulfates, alkyl polyglycosides and ethoxylated fatty alcohols, fatty acids, alkylphenols, sorbitan fatty esters and fatty alkanolamides; thickeners and gel formers, for example fatty alcohols, fatty acids, paraffin oils, fatty esters, methylcellulose, or hydroxyethylcellulose, starch, synthetic polymers such as polyvinylpyrrolidone and polyacrylates, or biopolymers such as alginic acid; stabilizers for peroxo compounds, for example silicates; as well as complexing agents; perfume oils and hair-care additives such as cationic polymers, lanolin derivatives, cholesterol, pantothenic acid, protein derivatives and protein hydrolyzates, provitamins and vitamins as well as plant extracts, alkali metal sulfates or alkaline earth metal sulfates, for example sodium sulfate and ammonium sulfate, alkali metal stearates or alkaline earth metal stearates, for example sodium stearate, and aluminum stearate. In the preparation of the oxidizing composition of the invention, these additives are used in amounts commonly employed for such purposes; for example the surfactants and emulsifiers are present at a concentration of from about 0.2 to 30 weight percent and the thickeners are present at a concentration of from about 0.1 to 30 weight percent relative to the total weight of the oxidizing composition.

The oxidizing composition of the invention is formulated, in admixture with the other components usually contained in bleaching agents, as a cosmetic composition in the form of a water-free powder or in a water-free, liquid or creamy medium ("coloring paste"). Powder formulations are usually dedusted by spraying with inert carrier materials, for example paraffin oils, silicone oils, polyethers, fatty esters, polyorganosiloxanes [for example with dimethylpolysiloxanes referred to in the International Cosmetic Ingredient Dictionary, 5th ed., pp. 220/221 (1993) under the name "dimethicone"] or waxes. Such dedusting methods are known, for example, from U.S. Pat. No. 5,698,186 and U.S. Pat. No. 5,891,423. Depending on the direct dye used, the dyes can also be in the form of an aqueous solution which is stored separately from the bleach powder and which is mixed with the oxidizing composition only just before use. The colorant can also be in a microencapsulated form or packaged in a water-soluble covering (for example in a polyvinyl alcohol or polyvinylpyrrolidone pouch) and released only upon mixing with the peroxide composition.

The Kit

The present invention may be provided as a kit to be used by the consumer or salon stylist. The kit comprises premeasured amounts of a first peroxide developer composition and a second bleach powder composition, along with instructions for use, preferably an applicator preferably with a tip for connection to the peroxide developer container, and gloves.

The peroxide developer may be provided in a container which also serves as the container for mixing the components and which together with applicator tip installed is used to apply the oxidizing composition to the hair. The peroxide developer component container has sufficient head space to allow for the mixing of the other components.

The bleach powder component is preferably contained in a foil pouch packet, the entire contents of which are emptied by the consumer into the developer component container.

The oxidizing composition applied to the hair preferably has a viscosity of from 20,000 to 60,000 cps, preferably from 30,000 to 45,000 cps. The product remains on the hair until the desired lightening of the hair is achieved. Generally, this period of time is less than about 60 minutes. The proportions of the three components used in the process are adapted so that there is no excess product or residual components of the product remaining after use. The proportions are predetermined so that the proper consistency of the product and the desired concentrations of the active ingredients as well as the adjuvants separately are contained in the final mixture composition once the six components (a), (b), (c), (d), (e) and (f) are mixed together and so that the final product pH would be from about 8.5 to about 13, preferably from about 9 to about 11.

The Method of Use

As described above the bleach powder composition is added from its packet into the peroxide developer, preferably in the applicator container. The contents are then mixed by shaking or stirring. Using the applicator tip, the final hair bleach product composition is applied to hair in conventional manner. The degree of lightening is checked periodically, and when the desired level of lightening is obtained, typically in less than 60 minutes even for black hair, the product is rinsed from the hair, and the hair is preferably shampooed and dried. Following rinsing, a hair conditioner, which may also be included in the kit, can be applied to the hair.

For professional stylist usage the bleach powder and peroxide developer will be provided in larger units e.g. a 1000 g can of the bleach powder and/or a 1000 ml bottle of peroxide developer. The ready to use oxidising composition will be mixed directly before use by a stylist in bowl or applicator bottle. The mixing ratio of the bleach powder to peroxide developer can be 2:1 up to 1:4.

The oxidising composition will be applied on the hair via applicator bottle or brush. It can be used full head and partly on single strands (highlight application). As common highlight applicator foils, caps and special applicators can be used, but also freehand techniques such as balayage, with brush and/or combs can be possible.

The Product Manufacture

The oxidizing composition of the present invention is manufactured by conventional processes known in the art for manufacturing bleaching and/or dyeing and/or permanent waving and/or relaxing/straightening products, and comprises ad-mixing the ingredients of each of the component compositions in suitable vessels, followed by packaging in appropriate individual containers.

EXAMPLES

The present invention is further illustrated by the examples that follow. Unless otherwise indicated all percentages referred to herein are percent by weight on an active ingredient basis of the mixed bleach powder-peroxide developer composition.

The following examples are oxidizing composition for bleaching of hair.

Bleach Powder Composition

Bleach powder 1: Bleach composition of Sasson white up (available from Wella professional) product.

Bleach powder 2: Bleach composition of Blondor (available from Wella professional) product.

Peroxide Developer Composition Examples:

| Ingredients | Comparative Example A | Comparative Example B | Comparative Example C | Invention Example D |
|---|---|---|---|---|
| Hydrogen Peroxide | 9% | 9% | 12% | 12% |
| Phosphoric Acid | 0.1 | 0.1 | 0.1 | 0.1 |
| Etidronic Acid | 0.05 | 0.05 | 0.05 | 0.05 |
| Cetylstearyl-alcohol | 3.5 | 3.5 | 3.5 | 3.5 |
| Ceteareth-25 | 0.2 | 0.2 | 0.2 | 0.2 |
| Sodium Laury Sulfate | 0.4 | 0.4 | 0.4 | 0.4 |
| Acrylates Copolymer | — | 3.0% | — | 1.0% |
| ACRYLATES/BEHENETH-25 METHACRYLATE COPOLYMER | — | — | 1.0% | 1.0% |
| Fragrance (optional) | — | — | — | — |
| Dimethicone | 0.05 | 0.05 | 0.05 | 0.05 |
| Water | Add to 100% | Add to 100% | Add to 100% | Add to 100% |

Resulting rheology measurements: Rheology for Hair Bleaches

Rheological Measurements

All measurements were conducted on a stress controlled rheometer (TA Instruments AR 2000 Rheometer & TA Instruments AR 2000) using a peltier plate and a flat acrylic plate geometry with 60 mm diameter (TA Instruments 516600.901).

Oscillatory Strain Sweep:

Sample preparation: Mix manually 10.0 g+/−0.1 g bleach powder composition with 30.0+/−0.1 g peroxide developer composition in an open bowel with a conventional hair color mixer for 1 min Let mixed sample rest for 5 min and then place it onto the rheometer. Lower geometry to target gap and trim edges.

Measurement: Temperature 23° C., Normal Force Controlled 0 N+/−0.3 N, starting geometry gap 1500 µm, Frequency 6.3 [rad/s], Sample conditioning on rheometer: 3 min at 23° C. Strain Sweep from 0.1% to 20%.

Oscillatory Frequency Sweep

Sample preparation: Mix manually 10.0 g+/−0.1 g bleach powder composition with 30.0+/−0.1 g peroxide developer composition in an open bowel with a conventional hair colour mixer for 1 min Let mixed sample rest for 5 min and then place it onto the rheometer. Lower geometry to target gap and trim edges.

Measurement: Temperature 23° C., Normal Force Controlled 0 N+/−0.5 N, starting geometry gap 1500 µm, Strain 0.2%

Sample conditioning on rheometer 3 min at 23° C.

Frequency Sweep from 0.1 to 100 Hz

Oscillatory Time Sweep

Sample Preparation:

Mix manually 10.0 g+/−0.1 g bleach powder composition with 30.0+/−0.1 g peroxide developer composition an open bowl with a conventional hair color mixer for 1 min Place it onto the rheometer, then lower geometry to target gap and trim edges.

Temperature 23° C., Normal Force Controlled 0 N+/−0.1 N, starting geometry gap 1500 µm, Strain 0.5%, Frequency: 6.3 [rad/s], Start measurement 4 min after mixing Frequency Sweep from 0.1 to 100 Hz Samples A Bleach 2+Developer A mixing ratio 1 to 3
B Bleach 2+Developer B mixing ratio 1 to 3
C Bleach 2+Developer C mixing ratio 1 to 3
D Bleach 2+Developer D mixing ratio 1 to 3

Results Strain Sweep: See Table Below and FIGS. 1a & b

| Strain | Bleach 1 | | | | Bleach 2 | | | |
|---|---|---|---|---|---|---|---|---|
| [%] | A | B | C | D | A | B | C | D |
| 0.4 | 466 | 501 | 463 | 1008 | 857 | 452 | 586 | 1205 |
| 0.5 | 442 | 486 | 454 | 1000 | 802 | 443 | 572 | 1200 |
| 0.6 | 416 | 470 | 440 | 990 | 740 | 432 | 554 | 1191 |
| 0.8 | 390 | 454 | 424 | 978 | 674 | 419 | 530 | 1177 |
| 1 | 364 | 437 | 404 | 963 | 610 | 405 | 499 | 1159 |
| 1.3 | 339 | 420 | 380 | 941 | 549 | 390 | 465 | 1133 |
| 1.6 | 314 | 402 | 353 | 914 | 491 | 373 | 425 | 1096 |
| 2 | 290 | 383 | 324 | 878 | 434 | 355 | 385 | 1040 |
| 2.6 | 266 | 363 | 294 | 825 | 389 | 334 | 345 | 930 |
| 3.2 | 243 | 340 | 262 | 742 | 347 | 312 | 305 | 808 |
| 4.1 | 219 | 317 | 231 | 646 | 308 | 288 | 269 | 702 |
| 5.2 | 196 | 291 | 203 | 568 | 273 | 263 | 237 | 601 |
| 6.6 | 173 | 265 | 176 | 495 | 243 | 237 | 205 | 506 |
| 8.3 | 152 | 238 | 152 | 432 | 214 | 211 | 178 | 417 |
| 10.5 | 132 | 211 | 130 | 376 | 186 | 185 | 153 | 349 |
| 10% drop | 419 | 451 | 417 | 907 | 771 | 407 | 528 | 1084 |

Conclusion

From the above data, it can be seen that the mixtures containing developer D show a high structural strength. They show with both bleaches a wider plateau value. The end of this plateau is defined by a drop of 10% of the first value (at 0.4% strain). They show a constant storage modulus value up to ~1.5% strain. In this plateau region, the hair bleach mixture does not change significantly the structure and gives a constant viscoelastic response. The end of the plateau value describes the strain exposure that is needed to destroy the structure of the gel network. Consequently, the mixtures containing developer D will tend to reduce dripping, reducing the tendency of the oxidizing composition to dry on the hair during application and/or on the brush during transport, from the bowl to the hair.

Figure 2A:
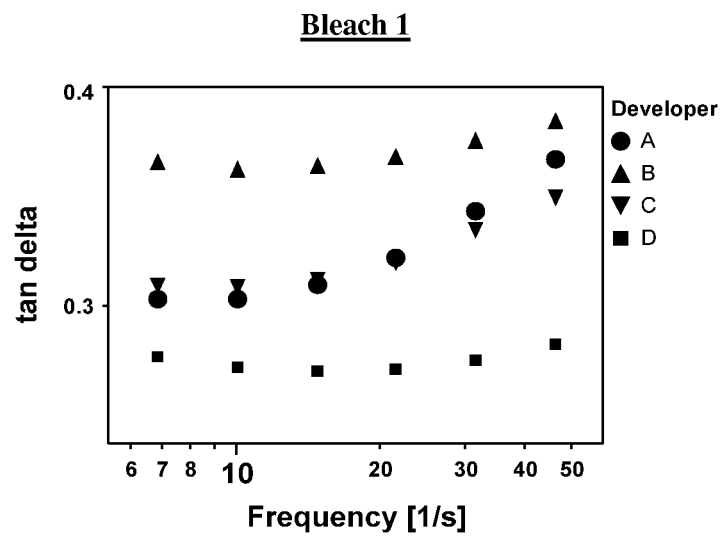
FIG. 2a show a graphical representation of frequency sweep curves resulting from a combination of bleach 1 and developers A, B, C and D.
Figure 2B:
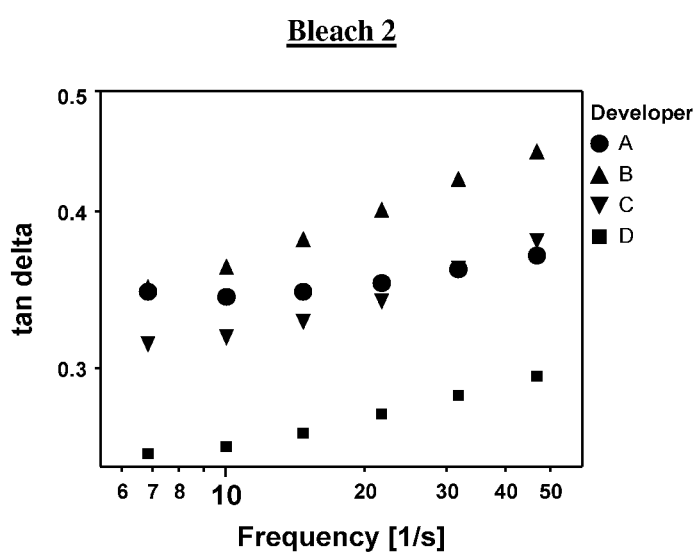
FIG. 2b show a graphical representation of frequency sweep curves resulting from a combination of bleach 2 and developers A, B, C and D.

Results Frequency Sweep and complex modulus G*: See Table Below and FIGS. 2a & b

| tan δ Frequency | Bleach 1 | | | | Bleach 2 | | | |
|---|---|---|---|---|---|---|---|---|
| [1/s] | A | B | C | D | A | B | C | D |
| 6.81 | 0.303 | 0.362 | 0.309 | 0.281 | 0.345 | 0.348 | 0.314 | 0.256 |
| 10 | 0.303 | 0.359 | 0.308 | 0.277 | 0.342 | 0.361 | 0.318 | 0.26 |
| 14.68 | 0.309 | 0.361 | 0.311 | 0.275 | 0.346 | 0.38 | 0.328 | 0.267 |
| 21.54 | 0.319 | 0.365 | 0.318 | 0.276 | 0.352 | 0.402 | 0.341 | 0.276 |

-continued

| tan δ Frequency | Bleach 1 | | | | Bleach 2 | | | |
|---|---|---|---|---|---|---|---|---|
| [1/s] | A | B | C | D | A | B | C | D |
| 31.62 | 0.34 | 0.373 | 0.332 | 0.28 | 0.361 | 0.425 | 0.362 | 0.285 |
| 46.4 | 0.364 | 0.382 | 0.346 | 0.286 | 0.37 | 0.448 | 0.38 | 0.296 |

It is estimated that for the application speed use with the Balayage technique the frequency range ~5-~50 [1/s] is equivalent. The mixtures containing developer D show over the frequency range ~5-~50 [1/s] a significantly lower loss factor [tan δ]. Therefore, they have a better elastic behaviour over the complete frequency range i.e. the mixtures have a more cohesive character.

| G* Frequency | Bleach 1 | | | | Bleach 2 | | | |
|---|---|---|---|---|---|---|---|---|
| [1/s] | A | B | C | D | A | B | C | D |
| 6.81 | 793 | 758 | 763 | 1609 | 1438 | 796 | 931 | 1795 |
| 10 | 840 | 818 | 819 | 1718 | 1534 | 858 | 999 | 1908 |
| 14.68 | 891 | 884 | 878 | 1834 | 1640 | 929 | 1074 | 2031 |
| 21.54 | 948 | 958 | 944 | 1953 | 1762 | 1013 | 1159 | 2169 |
| 31.62 | 1010 | 1040 | 1016 | 2088 | 1903 | 1112 | 1260 | 2327 |
| 46.4 | 1082 | 1139 | 1099 | 2233 | 2072 | 1226 | 1378 | 2516 |

Conclusion

The mixtures containing developer D show over the frequency range ~5-50 [1/s] a significantly higher complex modulus [G*]. Therefore, they show a stiffer material characteristic. Consequently, these mixtures provide a better application from brush onto the hair as the adhesive/cohesive ratio improves the stickiness to hair during application.

Figure 3A:
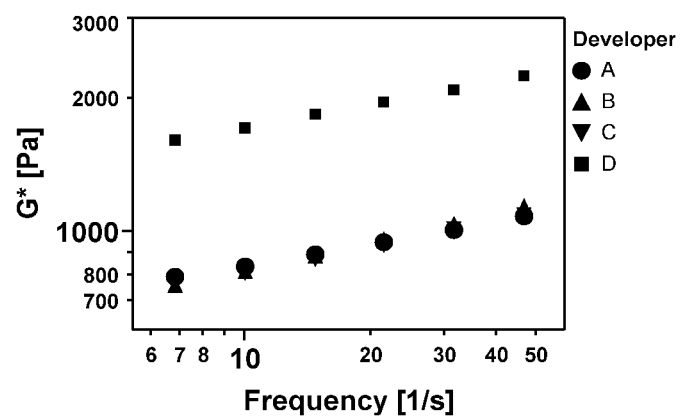
FIG. 3a shows a graphical representation of the complex modulus G* curves resulting from a combination of bleach 1 and developers A, B, C and D.
Figure 3B:
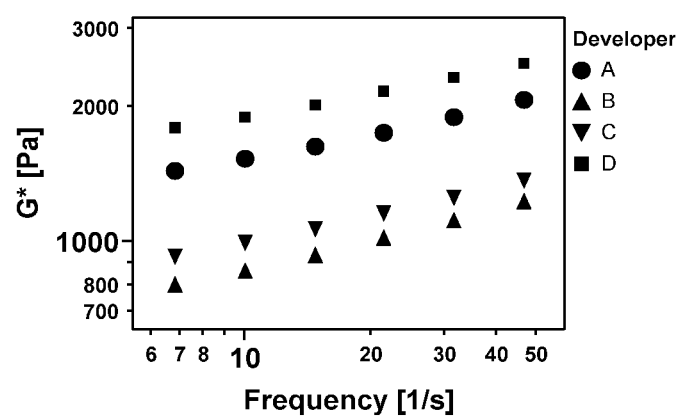
FIG. 3b shows a graphical representation of the complex modulus G* curves resulting from a combination of bleach 2 and developers A, B, C and D.

Results Volume increase: See Table Below and FIGS. 3a & b

Description of the procedure:

A certain amount of bleach powder and peroxide developer were mixed in a beaker (diameter: 60 mm) At the beginning (start) t=0, the beaker was filled a product with a combination ratio 1:3 of respectively bleach composition and developer. The surface of the beaker was marked where the surface of the product ended. A measurement, using a ruler was made from the bottom of the beaker until where the surface of the product ended. This measurement was made in mm using a ruler.

Then every 10 min the volume increase was marked up to 1 hour. The evolution of the volume increase was then measured at 10, 20 . . . 60 min in mm.

As shown above, the performance of the developer D has been tested first with bleach powder 1 and then second with bleach powder 2. In both cases, developer D showed less volume, when compared with developer A, B or D.

General Conclusion:

Practically the minimized swelling of the oxidizing composition described is convenient for the consumer and/or hairdresser. As an example, when used for highlighting partial sections of the hair; upon application of said oxidizing composition—due to the reduced swelling effect—the hair would deliver high lightening results on specific areas where the composition has been applied. Thus, it would avoid staining of the hair sections, not wished to be treated but positioned near the hair section where the oxidizing composition has been applied.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oxidizing composition for the treatment of keratin fibers, comprising;
    (a) from about 0.01% to about 8% of at least one anionic associative copolymer by weight of said composition;
    (b) at least one anionic non associative copolymer;
    (c) at least one peroxide agent;

| Product combination ratio: 1:3 | Start (mm) | 10 Min | 20 Min | 30 Min | 40 Min | 50 Min | 60 Min | Result after 60 min |
|---|---|---|---|---|---|---|---|---|
| Bleach 1 + developer B | 17 | 19 | 20 | 23 | 25 | 26 | 27 | 1.59 times of the start volume |
| Bleach 1 + developer D | 24 | 24 | 20 | 28 | 29 | 29 | 30 | 1.25 times of the start volume |
| Bleach 1 + developer A | 17 | 17 | 20 | 23 | 25 | 28 | 31 | 1.82 times of the start volume |
| Bleach 2 + developer D | 22 | 24 | 28 | 29 | 32 | 35 | 39 | 1.77 times of the start volume |
| Bleach 2 + developer A | 13 | 13 | 17 | 18 | 20 | 25 | 28 | 2.15 times of the start volume |
| Bleach powder (PLATINE PRECISION from l'Oréal) + developer (Oxydant (9%) from l'Oréal) | 13 | 14 | 17 | 19 | 22 | 25 | 28 | 2.15 times of the start volume |

(d) at least one persulfate agent;

(e) at least one alkalizing agent; and (f) a carrier medium suitable for keratin fibers.

2. The composition according to claim 1, wherein said anionic associative copolymer comprises a monomer having a carboxylic acid function and a monomer having an ester derived from a fatty alcohol and a carboxylic acid.

3. The composition according to claim 1, wherein said anionic non associative copolymer comprises a monomer having a carboxylic function and a monomer having an ester derived from an alkoxylated fatty alcohol and carboxylic acid.

4. The composition according to claim 1, wherein said composition comprises an anionic associative copolymer from about 0.05% to about 5%, by weight of the composition.

5. The composition according to claim 4, wherein said composition comprises an anionic associative copolymer from about 0.15% to about 2%, by weight of the composition.

6. The composition according to claim 1, wherein said composition comprises an anionic non associative copolymer from about 0.01% to about 8% by weight of said composition.

7. The composition according to claim 6, wherein said composition comprises an anionic non associative copolymer from about 0.05% to about 5%, by weight of the composition.

8. The composition according to claim 6, wherein said composition comprises an anionic non associative copolymer from about 0.15% to about 2%, by weight of the composition.

9. The composition according to claim 1, wherein the peroxide agent is selected from the group consisting of hydrogen peroxide, urea peroxide, melamine peroxide, and combinations thereof.

10. The composition according to claim 1, wherein said peroxide agent is present in said composition from about 0.6% to about 10.0% by weight of said composition.

11. The composition according to claim 1, wherein said persulfate agent is present from about 2.0% to about 30.0% by weight of said composition.

12. The composition according to claim 1, wherein said composition further comprises at least one cosmetic ingredient selected from the group consisting of dyes, chelants, hair care additives, paraffin oils, perfume oils and mixtures thereof.

13. A method for hair treatment comprising the steps of:

(i) providing a first mixture comprising at least one peroxide agent, at least one anionic associative copolymer, at least one anionic non associative copolymer, and a first carrier medium and;

(ii) providing a second mixture comprising at least one persulfate agent, at least one alkalizing agent, and a second carrier medium;

(iii) mixing the first mixture and the second mixture in order to obtain an oxidizing composition as defined in claim 1; and (iv) applying said oxidizing composition onto keratin fibers.

* * * * *